United States Patent
Kinoshita et al.

(10) Patent No.: US 12,415,055 B2
(45) Date of Patent: Sep. 16, 2025

(54) CATHETER ASSEMBLY AND MEDICAL VALVE

(71) Applicant: TERUMO KABUSHIKI KAISHA, Tokyo (JP)

(72) Inventors: Hideaki Kinoshita, Kofu (JP); Shota Yamamoto, Kai (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 76 days.

(21) Appl. No.: 16/789,828

(22) Filed: Feb. 13, 2020

(65) Prior Publication Data

US 2020/0179646 A1 Jun. 11, 2020

Related U.S. Application Data

(63) Continuation of application No. PCT/JP2018/036190, filed on Sep. 28, 2018.

(30) Foreign Application Priority Data

Sep. 29, 2017 (JP) .................................. 2017-191169

(51) Int. Cl.
*A61M 25/00* (2006.01)
*A61M 5/32* (2006.01)
(Continued)

(52) U.S. Cl.
CPC ........ *A61M 25/0097* (2013.01); *A61M 5/329* (2013.01); *A61M 25/0606* (2013.01);
(Continued)

(58) Field of Classification Search
CPC .......... A61M 25/0097; A61M 25/0606; A61M 25/0693; A61M 39/24; A61M 2039/2426;
(Continued)

(56) References Cited

U.S. PATENT DOCUMENTS 3,825,157 A * 7/1974 Herzig ..................... B65D 1/32
222/494
4,655,752 A 4/1987 Honkanen et al.
(Continued)

FOREIGN PATENT DOCUMENTS

EP 1911485 4/2008
EP 2638926 9/2013
(Continued)

OTHER PUBLICATIONS

International Preliminary Report on Patentability for International Application No. PCT/JP2018/036190, mailed Mar. 31, 2020.
(Continued)

*Primary Examiner* — William R Carpenter
*Assistant Examiner* — Robert F Allen
(74) *Attorney, Agent, or Firm* — Sheridan Ross P.C.

(57) ABSTRACT

A catheter assembly is provided with a catheter, a catheter hub, and a valve body (medical valve) provided in the catheter hub. The valve body includes a hollow main body provided with a distal end surface and a fixing portion for fixing the valve body to the catheter hub. At least a part of an outer peripheral surface and at least a part of an inner peripheral surface of the main body are inclined with respect to a central axis of the valve body. The main body of the valve body includes a distal end slit provided on the distal end surface and a side slit provided on the outer peripheral surface of the main body and continuously extending from the distal end slit.

4 Claims, 11 Drawing Sheets

(51) Int. Cl.
*A61M 25/06* (2006.01)
*A61M 39/06* (2006.01)
*A61M 39/24* (2006.01)

(52) U.S. Cl.
CPC ........ *A61M 25/0693* (2013.01); *A61M 39/24* (2013.01); *A61M 2025/0076* (2013.01); *A61M 2039/064* (2013.01); *A61M 2039/0646* (2013.01); *A61M 2039/066* (2013.01); *A61M 2039/0666* (2013.01); *A61M 39/0693* (2013.01); *A61M 2039/2426* (2013.01); *A61M 2039/2433* (2013.01); *A61M 2039/244* (2013.01)

(58) Field of Classification Search
CPC .......... A61M 39/06; A61M 2025/0076; A61M 2039/064; A61M 2039/0646; A61M 2039/0666; A61M 2039/2433; A61M 2039/244; A61M 2039/066; A61M 39/0693
See application file for complete search history.

(56) References Cited

U.S. PATENT DOCUMENTS

| | | | |
|---|---|---|---|
| 5,180,373 A | * | 1/1993 | Green ................ A61B 17/3498 251/149.1 |
| 5,261,459 A | * | 11/1993 | Atkinson .............. A61M 39/24 137/846 |
| 5,304,156 A | * | 4/1994 | Sylvanowicz .... A61M 39/0606 604/167.02 |
| 5,330,437 A | * | 7/1994 | Durman ................ A61M 39/06 137/846 |
| 5,814,026 A | * | 9/1998 | Yoon .................. A61B 17/3421 604/539 |
| 5,993,471 A | * | 11/1999 | Riza .................. A61B 17/3498 606/185 |
| 6,083,203 A | * | 7/2000 | Yoon .................. A61B 17/3421 604/167.01 |
| 7,396,346 B2 | | 7/2008 | Nakajima |
| 7,469,458 B1 | | 12/2008 | Starnes |
| 7,670,317 B2 | | 3/2010 | Cindirch et al. |
| 7,682,340 B2 | | 3/2010 | Funamura et al. |
| 7,691,090 B2 | | 4/2010 | Belley et al. |
| 7,695,458 B2 | | 4/2010 | Belley et al. |
| 7,806,869 B2 | | 10/2010 | Nilsson et al. |
| 7,938,806 B2 | | 5/2011 | Fisher et al. |
| 8,016,791 B2 | | 9/2011 | Sugiki et al. |
| 8,034,035 B2 | | 10/2011 | Weaver et al. |
| 8,048,033 B2 | | 11/2011 | Becker et al. |
| 8,048,039 B2 | | 11/2011 | Carlyon et al. |
| 8,062,261 B2 | | 11/2011 | Adams |
| 8,092,432 B2 | * | 1/2012 | Nordgren .............. A61M 39/24 604/537 |
| 8,096,976 B2 | | 1/2012 | Sugiki et al. |
| 8,105,287 B2 | | 1/2012 | Fisher et al. |
| 8,109,909 B2 | | 2/2012 | Tanabe et al. |
| 8,142,446 B2 | | 3/2012 | Shan |
| 8,251,923 B2 | | 8/2012 | Carrez et al. |
| 8,267,897 B2 | | 9/2012 | Wells |
| 8,286,657 B2 | | 10/2012 | Belley et al. |
| 8,317,754 B2 | | 11/2012 | Leeflang et al. |
| 8,357,119 B2 | | 1/2013 | Stout et al. |
| 8,361,020 B2 | | 1/2013 | Stout |
| 8,361,038 B2 | | 1/2013 | McKinnon et al. |
| 8,366,684 B2 | | 2/2013 | Harding |
| 8,377,011 B2 | | 2/2013 | Weaver et al. |
| 8,388,583 B2 | | 3/2013 | Stout et al. |
| 8,469,928 B2 | | 6/2013 | Stout et al. |
| 8,500,696 B2 | | 8/2013 | Kobayashi et al. |
| 8,512,293 B2 | | 8/2013 | Leeflang et al. |
| 8,574,203 B2 | | 11/2013 | Stout et al. |
| 8,585,651 B2 | | 11/2013 | Asai |
| 8,622,967 B2 | | 1/2014 | Davis et al. |
| 8,622,972 B2 | | 1/2014 | Nystrom et al. |
| 8,636,695 B2 | | 1/2014 | Cluff et al. |
| 8,641,675 B2 | | 2/2014 | Stout et al. |
| 8,652,104 B2 | | 2/2014 | Goral et al. |
| 8,690,833 B2 | | 4/2014 | Belson |
| 8,715,242 B2 | | 5/2014 | Helm, Jr. |
| 8,740,859 B2 | | 6/2014 | McKinnon et al. |
| 8,747,387 B2 | | 6/2014 | Belley et al. |
| 8,814,833 B2 | | 8/2014 | Farrell et al. |
| 8,864,715 B2 | | 10/2014 | Cluff et al. |
| 8,932,258 B2 | | 1/2015 | Blanchard et al. |
| 8,932,259 B2 | | 1/2015 | Stout et al. |
| 8,939,938 B2 | | 1/2015 | Funamura et al. |
| 8,951,230 B2 | | 2/2015 | Tanabe et al. |
| 8,998,852 B2 | | 4/2015 | Blanchard et al. |
| 9,017,288 B1 | | 4/2015 | Starnes |
| 9,052,025 B2 | | 6/2015 | Zinn et al. |
| 9,089,671 B2 | | 7/2015 | Stout et al. |
| 9,095,679 B2 | | 8/2015 | Nishimura et al. |
| 9,101,746 B2 | | 8/2015 | Stout et al. |
| 9,101,748 B2 | | 8/2015 | Harding et al. |
| 9,101,749 B2 | | 8/2015 | Nakagami et al. |
| 9,108,021 B2 | | 8/2015 | Hyer et al. |
| 9,114,241 B2 | | 8/2015 | Stout et al. |
| 9,126,012 B2 | | 9/2015 | McKinnon et al. |
| 9,155,863 B2 | | 10/2015 | Isaacson et al. |
| 9,155,864 B2 | | 10/2015 | Stout et al. |
| 9,155,876 B2 | | 10/2015 | Sonderegger et al. |
| 9,192,752 B2 | | 11/2015 | Leeflang et al. |
| 9,220,882 B2 | | 12/2015 | Belley et al. |
| 9,227,047 B2 | | 1/2016 | Khalaj |
| 9,233,230 B2 | | 1/2016 | Puhasm et al. |
| 9,242,071 B2 | | 1/2016 | Morgan et al. |
| 9,242,072 B2 | | 1/2016 | Morgan et al. |
| RE45,896 E | | 2/2016 | Stout et al. |
| 9,259,554 B2 | | 2/2016 | Ma et al. |
| 9,272,088 B2 | | 3/2016 | Bornhoft |
| 9,327,095 B2 | | 5/2016 | Ma |
| 9,352,119 B2 | | 5/2016 | Burkholz et al. |
| 9,352,127 B2 | | 5/2016 | Yeh et al. |
| 9,358,364 B2 | | 6/2016 | Isaacson et al. |
| 9,381,320 B2 | | 7/2016 | Vincent et al. |
| 9,399,116 B2 | | 7/2016 | Goral et al. |
| 9,408,569 B2 | | 8/2016 | Andreae et al. |
| 9,486,162 B2 | | 11/2016 | Zhuang et al. |
| 9,522,254 B2 | | 12/2016 | Belson |
| 9,545,495 B2 | | 1/2017 | Goral et al. |
| 9,579,486 B2 | | 2/2017 | Burkholz et al. |
| 9,579,490 B2 | | 2/2017 | Ma et al. |
| 9,592,367 B2 | | 3/2017 | Harding et al. |
| 9,604,030 B2 | | 3/2017 | Leeflang et al. |
| 9,604,035 B2 | | 3/2017 | Keyser et al. |
| 9,616,201 B2 | | 4/2017 | Belson |
| 9,737,686 B2 | | 8/2017 | Trainer et al. |
| 9,750,920 B2 | | 9/2017 | Vincent et al. |
| 9,750,925 B2 | | 9/2017 | Ma et al. |
| 9,750,927 B2 | | 9/2017 | Ma |
| 9,750,928 B2 | | 9/2017 | Burkholz et al. |
| 9,757,540 B2 | | 9/2017 | Belson |
| 9,770,580 B2 | | 9/2017 | Burkholz et al. |
| 9,775,972 B2 | | 10/2017 | Christensen et al. |
| 9,788,943 B2 | | 10/2017 | Deshmukh et al. |
| 9,789,280 B2 | | 10/2017 | Ma |
| 9,895,525 B2 | | 2/2018 | Ma et al. |
| 9,919,136 B2 | | 3/2018 | Lim et al. |
| 9,931,101 B2 | | 4/2018 | Okubo et al. |
| 9,937,322 B2 | | 4/2018 | Drake et al. |
| 9,943,677 B2 | | 4/2018 | Gordon et al. |
| 9,950,139 B2 | | 4/2018 | Blanchard et al. |
| 9,974,938 B2 | | 5/2018 | Pepin et al. |
| 9,999,746 B2 | | 6/2018 | Lareau et al. |
| 9,999,761 B2 | | 6/2018 | Joseph et al. |
| 10,052,474 B2 | | 8/2018 | Keyser et al. |
| 10,080,867 B2 | | 9/2018 | Goral et al. |
| 10,086,171 B2 | | 10/2018 | Belson |
| 10,105,085 B2 | | 10/2018 | Andreae et al. |
| 10,118,017 B2 | | 11/2018 | Isaacson et al. |
| 10,118,023 B2 | | 11/2018 | Yeh et al. |
| 10,159,820 B2 | | 12/2018 | Hall et al. |

(56) References Cited

U.S. PATENT DOCUMENTS

| | | |
|---|---|---|
| 10,188,845 B2 | 1/2019 | Fischer et al. |
| 10,238,852 B2 | 3/2019 | Burkholz et al. |
| 10,238,853 B2 | 3/2019 | Kume et al. |
| 10,265,506 B2 | 4/2019 | Borowicz |
| 10,286,185 B2 | 5/2019 | Tanabe et al. |
| 10,321,933 B1 | 6/2019 | Ramee et al. |
| 10,328,239 B2 | 6/2019 | Belson |
| 10,357,635 B2 | 7/2019 | Korkuch et al. |
| 10,426,929 B2 | 10/2019 | Burkholz et al. |
| 10,426,931 B2 | 10/2019 | Blanchard et al. |
| 10,441,773 B2 | 10/2019 | Ma et al. |
| 10,463,840 B2 | 11/2019 | Hyer et al. |
| 10,463,846 B2 | 11/2019 | Gordon et al. |
| 10,478,593 B2 | 11/2019 | Jones et al. |
| 10,478,609 B2 | 11/2019 | Harding et al. |
| 10,493,262 B2 | 12/2019 | Tran et al. |
| 10,500,329 B2 | 12/2019 | Weaver et al. |
| 10,500,376 B2 | 12/2019 | Isaacson et al. |
| 10,507,281 B2 | 12/2019 | Burkholz et al. |
| 10,512,755 B2 | 12/2019 | Hu et al. |
| 10,525,236 B2 | 1/2020 | Belson |
| 10,543,351 B2 | 1/2020 | Ma et al. |
| 10,543,354 B2 | 1/2020 | Bihlmaier et al. |
| 10,549,073 B2 | 2/2020 | Burkholz et al. |
| 10,596,351 B2 | 3/2020 | Liska |
| 10,617,859 B2 | 4/2020 | Lorimer et al. |
| 10,668,266 B2 | 6/2020 | Lin et al. |
| 10,675,440 B2 | 6/2020 | Abitabilo et al. |
| 10,688,280 B2 | 6/2020 | Blanchard et al. |
| 10,709,828 B2 | 7/2020 | Toellner et al. |
| 10,729,881 B2 | 8/2020 | Lareau et al. |
| 10,729,882 B2 | 8/2020 | Morgan et al. |
| 10,737,085 B2 | 8/2020 | Rieckmann et al. |
| 10,765,853 B2 | 9/2020 | Neff et al. |
| 10,799,680 B2 | 10/2020 | Belson |
| 10,835,729 B2 | 11/2020 | Agrawal et al. |
| 10,850,069 B2 | 12/2020 | Solomon |
| 10,850,070 B2 | 12/2020 | Naing et al. |
| 10,869,993 B2 | 12/2020 | Ma et al. |
| 10,898,223 B2 | 1/2021 | Harding et al. |
| 10,905,858 B2 | 2/2021 | Farrell et al. |
| 10,926,063 B2 | 2/2021 | Cupelli et al. |
| 10,933,217 B2 | 3/2021 | Blackman et al. |
| 10,994,101 B2 | 5/2021 | Ma et al. |
| 11,000,678 B2 | 5/2021 | Hall |
| 11,033,713 B2 | 6/2021 | Leeflang |
| 11,033,718 B2 | 6/2021 | Belson |
| 11,116,936 B2 | 9/2021 | Harding et al. |
| 11,135,399 B2 | 10/2021 | Isaacson et al. |
| 11,135,406 B2 | 10/2021 | Ribelin et al. |
| 11,147,957 B2 | 10/2021 | Burkholz et al. |
| 11,191,938 B2 | 12/2021 | Snow |
| 11,202,886 B2 | 12/2021 | Belson |
| 11,207,495 B2 | 12/2021 | Goral et al. |
| 11,213,656 B2 | 1/2022 | Garrison et al. |
| 11,219,747 B2 | 1/2022 | Breindel et al. |
| 11,224,720 B2 | 1/2022 | Brunetti |
| 11,229,730 B2 | 1/2022 | Teo et al. |
| 11,260,146 B2 | 3/2022 | Busam et al. |
| 11,291,802 B2 | 4/2022 | Naidu et al. |
| 11,291,803 B2 | 4/2022 | Burkholz et al. |
| 11,291,805 B2 | 4/2022 | Ouchi et al. |
| 11,324,919 B2 | 5/2022 | Ma |
| 11,324,922 B2 | 5/2022 | Trainer et al. |
| 11,324,926 B2 | 5/2022 | Harding |
| 11,324,927 B2 | 5/2022 | Cheng |
| 11,324,939 B2 | 5/2022 | Solomon et al. |
| 11,338,113 B2 | 5/2022 | Isaacson et al. |
| 11,357,962 B2 | 6/2022 | Burkholz et al. |
| 11,389,624 B2 | 7/2022 | Cook |
| 11,406,810 B2 | 8/2022 | Harding et al. |
| 11,413,432 B2 | 8/2022 | Hyer et al. |
| 11,420,025 B2 | 8/2022 | Thirumoorthy et al. |
| 11,420,034 B2 | 8/2022 | Solomon et al. |
| 11,433,226 B2 | 9/2022 | Kume et al. |
| 11,439,794 B2 | 9/2022 | Ebner et al. |
| 11,446,467 B2 | 9/2022 | Breindel et al. |
| 11,446,472 B2 | 9/2022 | Kumar et al. |
| 11,452,847 B1 | 9/2022 | Cook |
| 11,452,858 B2 | 9/2022 | Keyser et al. |
| 11,478,610 B2 | 10/2022 | Vincent et al. |
| 11,504,500 B2 | 11/2022 | Naidu et al. |
| 11,511,098 B2 | 11/2022 | Agrawal et al. |
| 11,524,152 B1 | 12/2022 | Leeflang et al. |
| 11,529,474 B2 | 12/2022 | Nakagami et al. |
| 11,534,581 B2 | 12/2022 | Isaacson et al. |
| 11,534,591 B2 | 12/2022 | Hu et al. |
| 2004/0158208 A1* | 8/2004 | Hiejima ............. A61M 39/26 604/167.04 |
| 2005/0187524 A1* | 8/2005 | Willis ............... A61M 39/26 604/256 |
| 2006/0155245 A1* | 7/2006 | Woehr ........... A61M 25/0606 604/110 |
| 2006/0253084 A1* | 11/2006 | Nordgren ............ F16K 15/147 604/247 |
| 2008/0082082 A1* | 4/2008 | Carlyon ......... A61M 25/0606 604/523 |
| 2008/0108944 A1* | 5/2008 | Woehr ........... A61B 5/150389 604/164.08 |
| 2008/0208132 A1* | 8/2008 | Funamura ......... A61M 39/0693 604/167.03 |
| 2009/0259175 A1* | 10/2009 | Nordgren ............ F16K 15/147 604/30 |
| 2011/0160663 A1* | 6/2011 | Stout ............. A61M 25/0693 604/122 |
| 2012/0232499 A1* | 9/2012 | Stout ............. A61M 25/0637 604/256 |
| 2013/0090609 A1* | 4/2013 | Sonderegger ........ A61M 39/24 604/256 |
| 2013/0165868 A1* | 6/2013 | Isaacson ......... A61M 25/0693 29/428 |
| 2013/0204226 A1* | 8/2013 | Keyser ............ A61M 25/0097 137/511 |
| 2014/0074034 A1* | 3/2014 | Tanabe ........... A61M 25/0097 604/167.03 |
| 2015/0151088 A1* | 6/2015 | Lim ............... A61M 25/0693 604/247 |
| 2015/0305863 A1 | 10/2015 | Gray et al. |
| 2015/0306349 A1* | 10/2015 | Bonnal ........... A61M 25/0097 604/272 |
| 2017/0120010 A1* | 5/2017 | Burkholz ......... A61M 25/0631 |
| 2017/0354799 A1* | 12/2017 | Gupta ............. A61M 25/0606 |
| 2018/0361119 A1 | 12/2018 | Goral et al. |
| 2018/0361120 A1 | 12/2018 | Goral et al. |
| 2019/0001031 A1 | 1/2019 | Real et al. |
| 2019/0160258 A1 | 5/2019 | Kreisten |
| 2019/0167966 A1 | 6/2019 | Burkholz et al. |
| 2019/0388653 A1 | 12/2019 | Breindel et al. |
| 2020/0046946 A1 | 2/2020 | Staley et al. |
| 2020/0061279 A1 | 2/2020 | Weaver et al. |
| 2020/0078515 A1 | 3/2020 | Burkholz et al. |
| 2020/0078556 A1 | 3/2020 | Hu et al. |
| 2020/0094024 A1 | 3/2020 | Teoh |
| 2020/0094037 A1 | 3/2020 | Tran et al. |
| 2020/0101265 A1 | 4/2020 | Burkholz et al. |
| 2020/0121896 A1 | 4/2020 | Baid |
| 2020/0155809 A1 | 5/2020 | Burkholz et al. |
| 2020/0179613 A1 | 6/2020 | Branson et al. |
| 2020/0261702 A1 | 8/2020 | Jewell et al. |
| 2020/0297969 A1 | 9/2020 | Abitabilo et al. |
| 2020/0297989 A1 | 9/2020 | Rieckmann et al. |
| 2020/0316347 A1 | 10/2020 | Belson |
| 2020/0324088 A1 | 10/2020 | Harding et al. |
| 2020/0405275 A1 | 12/2020 | Abitabilo et al. |
| 2021/0023358 A1 | 1/2021 | Agrawal et al. |
| 2021/0031008 A1 | 2/2021 | Woehr et al. |
| 2021/0031009 A1 | 2/2021 | Solomon |
| 2021/0038868 A1 | 2/2021 | Naing et al. |
| 2021/0052879 A1 | 2/2021 | Spataro |
| 2021/0068731 A1 | 3/2021 | Kumar |
| 2021/0068732 A1 | 3/2021 | Yan et al. |
| 2021/0069476 A1 | 3/2021 | Ma et al. |
| 2021/0106356 A1 | 4/2021 | Harding et al. |

(56) References Cited

U.S. PATENT DOCUMENTS

| | | |
|---|---|---|
| 2021/0113824 A1 | 4/2021 | Chng et al. |
| 2021/0146110 A1 | 5/2021 | Nelson et al. |
| 2021/0154439 A1 | 5/2021 | Blanchard et al. |
| 2021/0220619 A1 | 7/2021 | Farrell et al. |
| 2021/0228781 A1 | 7/2021 | Scherich et al. |
| 2021/0236790 A1 | 8/2021 | Kume et al. |
| 2021/0283376 A1 | 9/2021 | Yamamoto et al. |
| 2021/0299425 A1 | 9/2021 | Kume et al. |
| 2021/0299429 A1 | 9/2021 | Naidu et al. |
| 2021/0346653 A1 | 11/2021 | Burkholz et al. |
| 2021/0361911 A1 | 11/2021 | Isaacson et al. |
| 2021/0370020 A1 | 12/2021 | Gupta |
| 2021/0379337 A1 | 12/2021 | Yamamoto et al. |
| 2021/0393918 A1 | 12/2021 | Rasmussen et al. |
| 2021/0393920 A1 | 12/2021 | Yamamoto et al. |
| 2021/0402143 A1 | 12/2021 | Yokota et al. |
| 2022/0001161 A1 | 1/2022 | Burkholz et al. |
| 2022/0023592 A1 | 1/2022 | Scherich et al. |
| 2022/0080159 A1 | 3/2022 | Garrison et al. |
| 2022/0088360 A1 | 3/2022 | Snow |
| 2022/0111191 A1 | 4/2022 | Ma |
| 2022/0152359 A1 | 5/2022 | Naidu et al. |
| 2022/0161003 A1 | 5/2022 | Cook |
| 2022/0168548 A1 | 6/2022 | Dong |
| 2022/0176080 A1 | 6/2022 | Ng et al. |
| 2022/0225914 A1 | 7/2022 | Chen et al. |
| 2022/0226631 A1 | 7/2022 | Natesan |
| 2022/0233813 A1 | 7/2022 | Ma |
| 2022/0233816 A1 | 7/2022 | Muskatello et al. |
| 2022/0233817 A1 | 7/2022 | Trainer et al. |
| 2022/0233822 A1 | 7/2022 | Cheng |
| 2022/0233823 A1 | 7/2022 | Harding |
| 2022/0265986 A1 | 8/2022 | Burkholz et al. |
| 2022/0280757 A1 | 9/2022 | Wada et al. |
| 2022/0280767 A1 | 9/2022 | Solomon et al. |
| 2022/0296859 A1 | 9/2022 | Sutton et al. |
| 2022/0313959 A1 | 10/2022 | Cook |
| 2022/0322984 A1 | 10/2022 | Millerd |
| 2022/0339420 A1 | 10/2022 | Harding et al. |
| 2022/0355081 A1 | 11/2022 | Thirumoorthy et al. |
| 2022/0355093 A1 | 11/2022 | Natesan et al. |
| 2022/0362510 A1 | 11/2022 | Lackey et al. |
| 2022/0362516 A1 | 11/2022 | Lackey et al. |
| 2022/0362523 A1 | 11/2022 | Huang et al. |
| 2022/0370764 A1 | 11/2022 | Ebner et al. |
| 2022/0370765 A1 | 11/2022 | Lackey et al. |
| 2022/0379088 A1 | 12/2022 | Scherich et al. |
| 2022/0379103 A1 | 12/2022 | Chen et al. |
| 2022/0387762 A1 | 12/2022 | Kumar et al. |
| 2022/0401717 A1 | 12/2022 | Bihlmaier et al. |
| 2022/0409864 A1 | 12/2022 | Kinoshita |
| 2023/0012604 A1 | 1/2023 | Vincent et al. |

FOREIGN PATENT DOCUMENTS

| | | | | |
|---|---|---|---|---|
| EP | 2398545 | 4/2015 | | |
| EP | 3266490 | 1/2018 | | |
| EP | 3381495 | 10/2018 | | |
| EP | 2593166 | 12/2018 | | |
| EP | 3466479 | 4/2019 | | |
| EP | 3470106 | 4/2019 | | |
| EP | 2763740 | 5/2019 | | |
| EP | 3082933 | 6/2019 | | |
| EP | 3337549 | 6/2019 | | |
| EP | 3532128 | 9/2019 | | |
| EP | 3552652 | 10/2019 | | |
| EP | 2310080 | 4/2020 | | |
| EP | 3283155 | 9/2020 | | |
| EP | 3717046 | 10/2020 | | |
| EP | 3911395 | 11/2021 | | |
| EP | 3967344 | 3/2022 | | |
| EP | 3893984 | 1/2024 | | |
| EP | 3509513 | 8/2024 | | |
| JP | H 02-164376 A | 6/1990 | | |
| JP | 2000-279527 A | 10/2000 | | |
| JP | 3486188 | 1/2004 | | |
| JP | 4510619 | 7/2010 | | |
| JP | 4538471 | 9/2010 | | |
| JP | 3167575 | 4/2011 | | |
| JP | 2011-115630 A | 6/2011 | | |
| JP | 4964592 | 7/2012 | | |
| JP | 4996015 | 8/2012 | | |
| JP | 5253534 | 7/2013 | | |
| JP | 5591833 | 9/2014 | | |
| JP | 2014-528807 | 10/2014 | | |
| JP | 2014-528808 | 10/2014 | | |
| JP | 5603406 | 10/2014 | | |
| JP | 2015-511149 A | 4/2015 | | |
| JP | 5813764 | 11/2015 | | |
| JP | 5813765 | 11/2015 | | |
| JP | 2016-526469 | 9/2016 | | |
| JP | 2016-527027 | 9/2016 | | |
| JP | 5997900 | 9/2016 | | |
| JP | 6147186 | 6/2017 | | |
| JP | 2017-518150 A | 7/2017 | | |
| JP | 2019-162452 | 9/2019 | | |
| JP | 6752814 | 9/2020 | | |
| WO | WO 2016/163939 | 10/2016 | | |
| WO | WO-2016168745 A1 * | 10/2016 | ........ | A61M 25/0029 |
| WO | WO 2017/009483 | 1/2017 | | |
| WO | WO-2017029361 A1 * | 2/2017 | ......... | A61B 5/15003 |
| WO | WO 2017/042825 | 3/2017 | | |
| WO | WO 2017/044029 | 3/2017 | | |
| WO | WO 2017/081226 | 5/2017 | | |
| WO | WO 2017/106673 | 6/2017 | | |
| WO | WO 2022/029190 | 2/2022 | | |
| WO | WO 2022/118837 | 6/2022 | | |
| WO | WO 2022/220331 | 10/2022 | | |
| WO | WO 2022/220332 | 10/2022 | | |
| WO | WO 2022/240594 | 11/2022 | | |
| WO | WO 2022/241189 | 11/2022 | | |
| WO | WO 2022/241193 | 11/2022 | | |
| WO | WO 2022/245703 | 11/2022 | | |
| WO | WO 2022/250931 | 12/2022 | | |
| WO | WO 2022/251015 | 12/2022 | | |

OTHER PUBLICATIONS

International Search Report for International Application No. PCT/JP2018/036190, mailed Oct. 23, 2018.

Written Opinion for International Application No. PCT/JP2018/036190, mailed Oct. 23, 2018.

International Preliminary Report on Patentability (Including Translation) for International Application No. PCT/JP2018/036190, mailed Mar. 31, 2020.

Notice of Reasons for Refusal (Including Translation) for corresponding Japanese Patent Application No. 2019-545667, mailed Nov. 1, 2022.

* cited by examiner

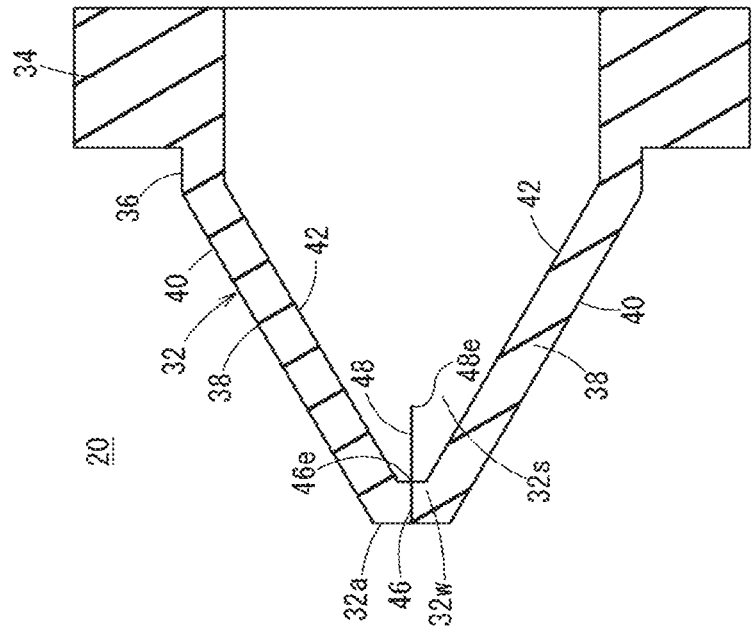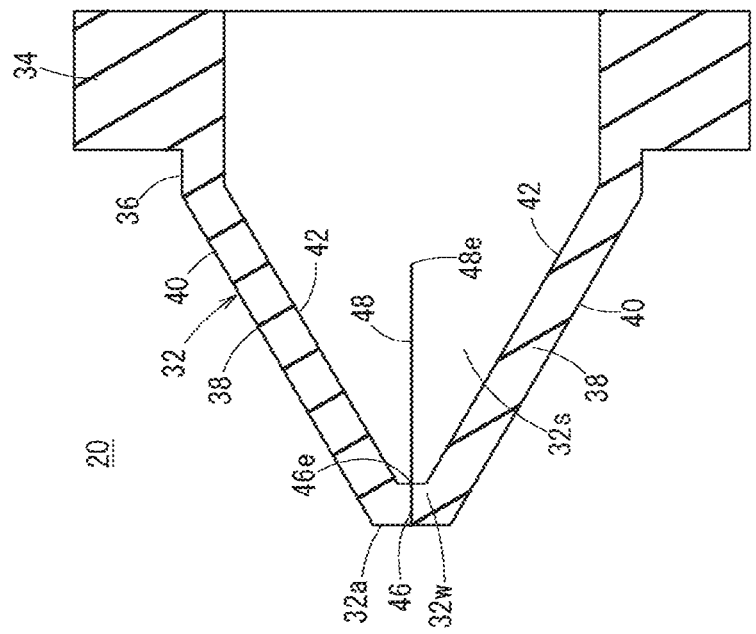

CATHETER ASSEMBLY AND MEDICAL VALVE

CROSS REFERENCE TO RELATED APPLICATIONS

The present application is a continuation of and claims benefit to PCT Application No. PCT/JP2018/036190, filed on Sep. 28, 2018, entitled "CATHETER ASSEMBLY AND MEDICAL VALVE" which claims priority to Japanese Patent Application No. 2017-191169, filed on Sep. 29, 2017. The entire disclosures of the applications listed above are hereby incorporated herein by reference, in their entirety, for all that they teach and for all purposes.

FIELD

The present disclosure relates to catheter assemblies, including catheters, with which a blood vessel is punctured for transfusion and the like to a patient. The present disclosure also relates to medical valves.

BACKGROUND

Conventionally, for example, a catheter assembly is used to perform transfusion or the like to a patient. This type of catheter assembly is provided with a catheter, a catheter hub fixed to a proximal end of the catheter, an inner needle inserted into the catheter, and a needle hub fixed to a proximal end of the inner needle. This type of catheter assembly includes one in which a valve is provided in the catheter hub in order to prevent a blood backflow (outflow of blood from the catheter hub) when the catheter is inserted into the body. As one mode of the valve, there is a so-called disc valve in which a slit is provided in a disc-shaped valve body. In a case of the disc valve, it is necessary to open the valve body by advancing a separate component referred to as a plug arranged in the catheter hub at the time of transfusion.

In contrast, there also is a type of assembly in which a duckbill valve (one-way valve) is provided in the catheter hub for the similar purpose (for example, refer to JP 2-164376 A). In a case of the duckbill valve, when blood flows into the catheter hub through the catheter, a blood pressure in a proximal direction is applied to the valve body to deform the same, so that the valve body is closed. On the contrary, when a drug solution is supplied from a proximal end side of the catheter hub, a pressure of the drug solution is applied to the valve body in a distal direction to deform the same, so that the valve body is opened. Therefore, in a case of the duckbill valve, the separate component for opening is not necessary.

SUMMARY

In a case of the conventional duckbill valve, the separate component for opening is not required, but there is a disadvantage that a flow rate of the drug solution is likely to be reduced because of a structure to open by using the pressure of the drug solution. It is desired that the valve body may be opened more easily even in a case where the separate component for opening is used.

A catheter assembly according to the present disclosure is provided with a catheter, a catheter hub fixed to the catheter, and a valve body provided in the catheter hub, in which the valve body includes a hollow main body provided with a distal end surface located at a distal end of the valve body and a fixing portion for fixing the valve body to the catheter hub, at least a part of an outer peripheral surface of the main body is inclined with respect to a central axis of the valve body, at least a part of an inner peripheral surface in an internal space of the main body is inclined with respect to the central axis, and the main body includes a distal end slit provided on the distal end surface and a side slit provided on the outer peripheral surface of the main body and continuously extending from the distal end slit.

In one embodiment of the present disclosure, configured as described above, the main body of the valve body is provided with not only the distal end slit but also the side slit continuously extending from the distal end slit, so that the main body is easily deformed when the pressure (e.g., blood pressure or drug solution pressure, etc.) is applied to the main body. Therefore, when the blood pressure is applied to the main body from a distal end side, the main body is deformed inward and the distal end slit and the side slit close, so that a blood backflow may be suppressed. In contrast, when the drug solution pressure is applied to the main body from a proximal end side, the main body is deformed outward and not only the distal end slit but also the side slit opens, so that a flow rate at the time of opening may be increased. Therefore, according to the present disclosure, it is not necessary to use a separate component for opening the valve, and it is possible to increase the flow rate at the time of opening compared to the flow rate of a catheter assembly with a structure using a conventional duckbill valve.

A pair of side slits may be continuous from both ends in a slit length direction of the distal end slit.

With this configuration, when the pressure is applied from the distal end side or the proximal end side of the valve body, the main body is more easily deformed inward or outward. Therefore, a function as a check valve (e.g., a function of stopping or suppressing blood and/or a function of allowing a drug solution to flow, etc.) may be improved.

The valve body may include a cylindrical portion formed to be thinner than the fixing portion between the main body and the fixing portion. The cylindrical portion may be disposed between the main body and the fixing portion, or base. In one embodiment, the cylindrical portion may have an outer diameter that is less than an outer diameter of the fixing portion.

With this configuration, a proximal end of the main body is not directly connected to a distal end of the fixing portion but is connected to a thinner cylindrical portion, so that the main body is more easily deformed when the pressure is applied to the main body.

A proximal end of the side slit may be located at a proximal end of the cylindrical portion.

With this configuration, the main body is more easily deformed, so that the function as the check valve (e.g., the function of stopping or suppressing the blood and/or the function of allowing the drug solution to flow) may be improved.

The proximal end of the side slit may be located on a distal end side with respect to the proximal end of the main body.

The proximal end of the side slit may be located on a distal end side with respect to the distal end of the fixing portion.

The proximal end of the side slit may be located on a proximal end side with respect to a central position in an axial direction of the main body.

The proximal end of the side slit may be located on a distal end side with respect to the central position in the axial direction of the main body.

The catheter assembly may be provided with an inner needle inserting into the catheter, and in a state in which the inner needle inserts into, and/or through, the valve body, a gap may be formed between slit surfaces forming the distal end slit and an outer surface of the inner needle.

With this configuration, at the time of the puncture of the blood vessel with the distal end of the catheter assembly, it is possible to allow air to flow from the distal end side to the proximal end side of the valve body through the gap formed between the slit surfaces and the inner needle. As a result, the catheter hub may be vented before the inner needle is removed from the catheter, and the distal end side with respect to the valve body in the catheter hub may be filled with the blood.

A hollow opening member arranged in a lumen of the catheter hub which is displaceable in the distal direction with respect to the catheter hub to open the valve body may be provided.

With this configuration, it is possible to open the valve body even when a moving distance from when the opening member starts pushing the valve body is shorter than that in a case of a combination of a disc-shaped valve body (so-called disc valve) and the opening member. The valve body may be opened with a smaller force than that in a case of the combination of the disc-shaped valve body and the opening member, so that the operation is easy.

In a state in which the opening member opens the valve body, the distal end slit of the valve body may be deformed along an outer shape of the opening member, and a gap of the side slit may be widened in a distal direction.

A medical valve according to the present disclosure is provided with a hollow main body including a distal end surface, and a base located on a proximal end side of the main body, in which at least a part of an outer peripheral surface of the main body is inclined with respect to a central axis of the main body, at least a part of an inner peripheral surface in an internal space of the main body is inclined with respect to the central axis, and the main body includes a distal end slit provided on the distal end surface and a side slit provided on the outer peripheral surface of the main body and continuously extending from the distal end slit.

According to the catheter assembly and medical valve of the present disclosure, it is not necessary to use a separate component for opening the valve, and it is possible to increase the flow rate at the time of opening from that with a structure using a conventional duckbill valve.

BRIEF DESCRIPTION OF THE DRAWINGS

FIG. 5A is a cross-sectional view of a valve body illustrating an example in which a length of a side slit is made shorter than the slit of the valve body shown in FIG. 4;

FIG. 5B is a cross-sectional view of a valve body illustrating an example in which a length of the side slit is made further shorter than the slit of the valve body shown in FIG. 5A;

DETAILED DESCRIPTION

Embodiments of a catheter assembly and a medical valve according to the present disclosure are hereinafter described with reference to the accompanying drawings.

Figure 1:
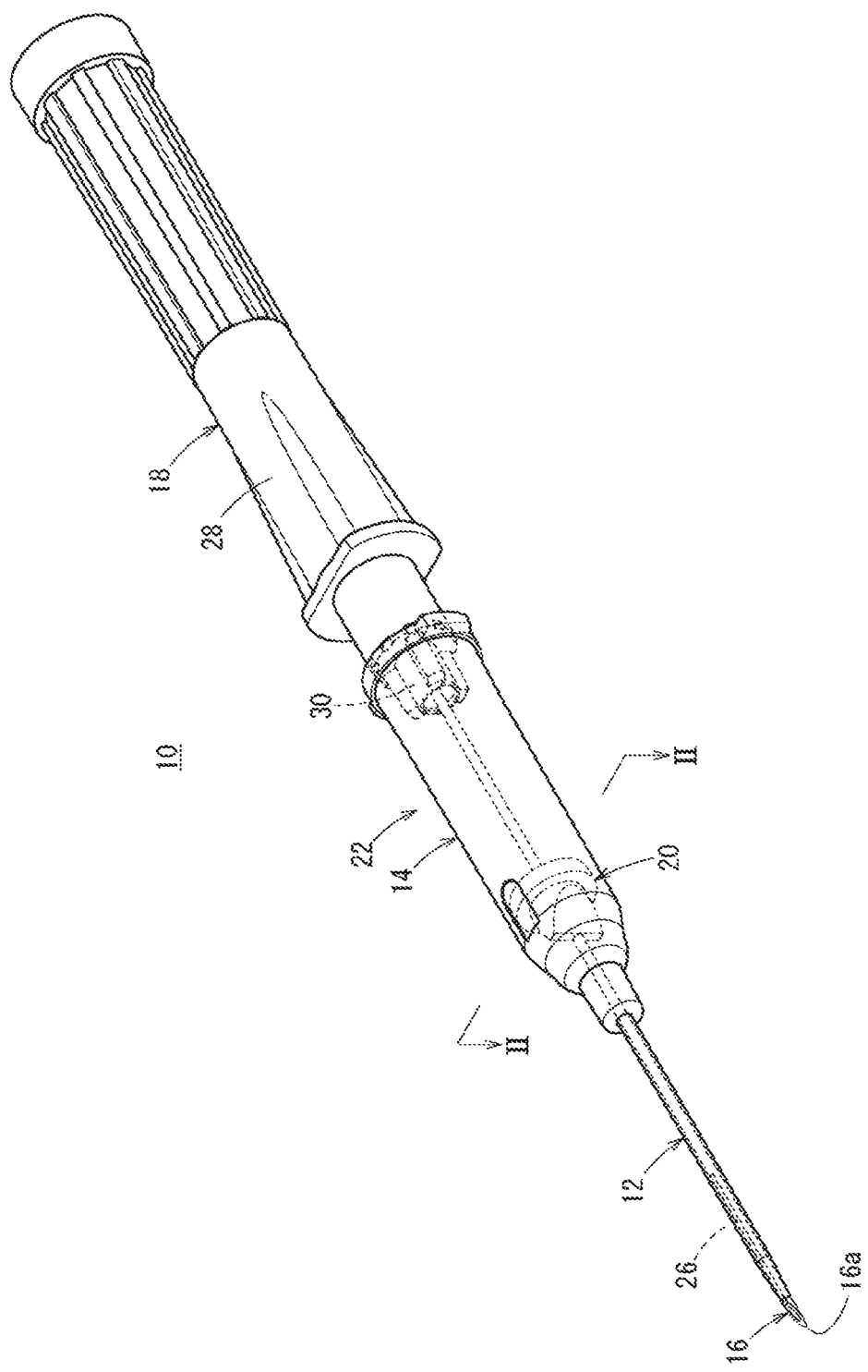
FIG. 1 is a perspective view of a catheter assembly according to an embodiment of the present disclosure.

Referring to FIG. 1, a catheter assembly 10 is illustrated comprising a catheter 12, a catheter hub 14 connected to a proximal end side of the catheter 12, an inner needle 16 including a sharp needle tip 16a at a distal end thereof, the inner needle 16 inserting into the catheter 12, a needle hub 18 connected to the inner needle 16, and a valve body 20 (e.g., a medical valve, etc.) arranged in the catheter hub 14.

The catheter assembly 10 is arranged such that the needle hub 18 can be gripped by a user (e.g., a doctor, nurse, medical worker, or the like), and a blood vessel of a patient is punctured with a distal end thereof. In an initial state before use (e.g., before puncture of the patient), the catheter assembly 10 has a double tube structure in which the inner needle 16 inserts into the catheter 12, and the inner needle 16 protrudes from a distal end of the catheter 12 by a predetermined length.

Figure 2:
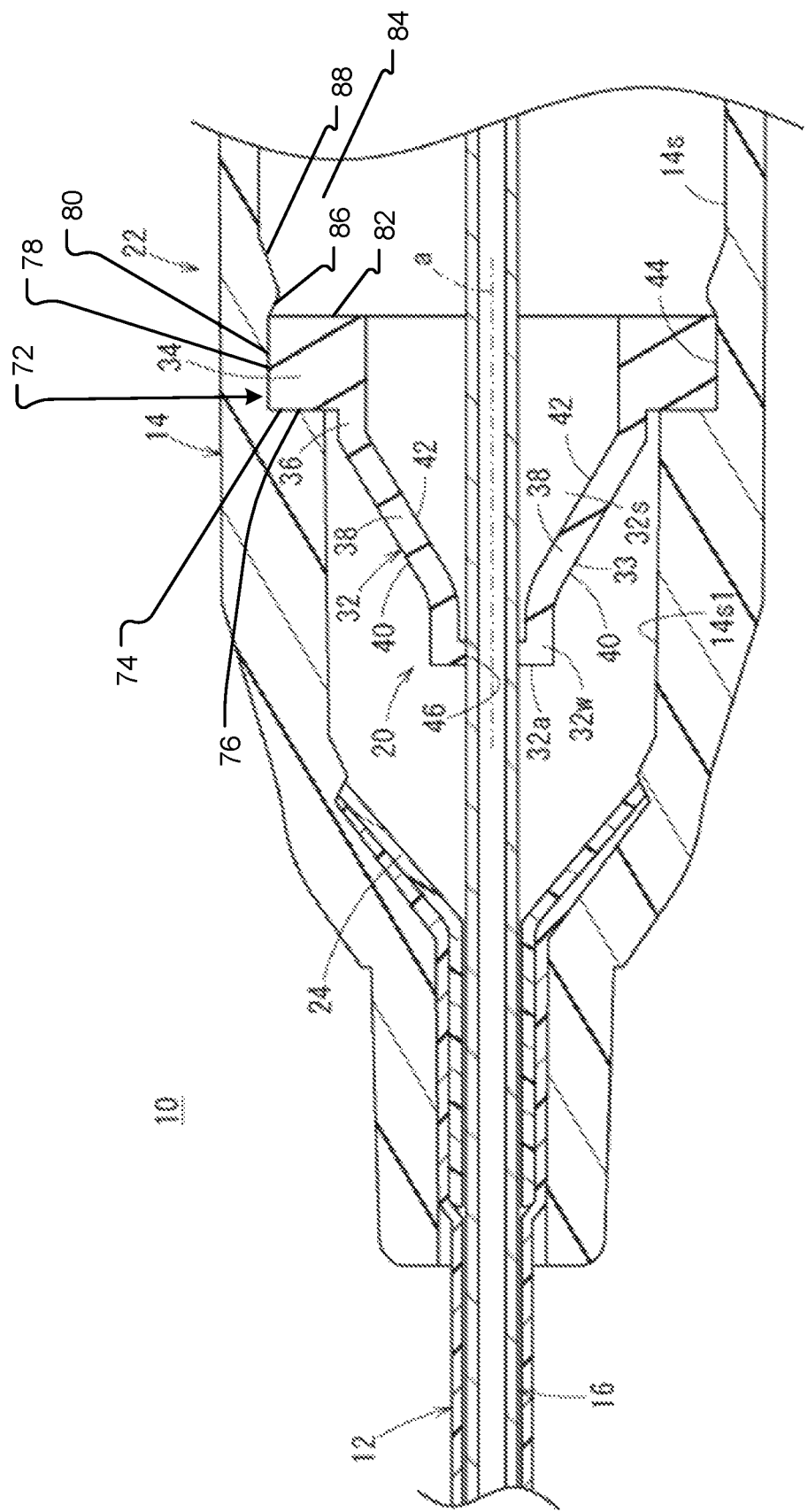
FIG. 2 is a partial cross-sectional view of the catheter assembly taken along line II-II in FIG. 1.

The catheter 12 is a small-diameter tubular member having flexibility. The catheter 12 may be formed of, for example, a resin material, preferably a soft resin material. A hollow catheter hub 14 is connected to be fixed to a proximal end of the catheter 12. The catheter 12, the catheter hub 14, and the valve body 20 form a catheter member 22. As illustrated in FIG. 2, the proximal end of the catheter 12 is fixed to a distal end of the catheter hub 14 by a fixing member 24 arranged in the distal end of the catheter hub 14.

When the catheter assembly 10 is used, the catheter hub 14 is exposed on a skin of the patient in a state in which the blood vessel is punctured with the catheter 12, and is adhered to the skin with a dressing material, a tape or the like to be indwelled thereon.

In FIG. 1, the inner needle 16 is a tubular member having rigidity capable of puncturing the skin of the patient, and is formed of, for example, a metal material (e.g., stainless steel or the like). On a top surface of a distal end of the inner needle 16, a groove 26 for checking blood flashback is formed. In the initial state of the catheter assembly 10 illustrated in FIG. 1, a proximal end of the inner needle 16 is arranged in a hollow portion of the catheter hub 14. Note that the inner needle 16 may also be formed as a solid needle.

The needle hub 18 is connected to the proximal end of the inner needle 16. The needle hub 18 includes a hub main body 28 which serves as a grip that is gripped by the user and a needle holder 30 which protrudes from the hub main body 28 in a distal direction and holds the proximal end of the inner needle 16. In the initial state of the catheter assembly 10, the needle holder 30 is inserted into a proximal end of the catheter hub 14.

The valve body 20 may correspond to a check valve (e.g., a one-way valve) which prevents a backflow of blood in a proximal direction (outflow of blood from the catheter hub 14) and allows passage of a drug solution in the distal direction. A material forming the valve body 20 may include, for example, a synthetic rubber such as polybutadiene series, nitrile series, and chloroprene series, a natural rubber such as polyisoprene, or a thermosetting elastomer such as urethane rubber, silicon rubber, and fluorine rubber, thermoplastic elastomer, or other elastomers.

As illustrated in FIG. 2, the valve body 20 is provided with a hollow main body 32 (e.g., the bill portion of the valve body 20) provided with a distal end surface 32a located at a distal end of the valve body 20, a fixing portion 34 provided on a proximal side with respect to the main body 32 for fixing the valve body 20 to the catheter hub 14, and a cylindrical portion 36 provided between the main body 32 and the fixing portion 34. The main body 32 and the cylindrical portion 36 protrude from the fixing portion 34 in the distal direction, that is, toward the catheter 12. In the initial state of the catheter assembly 10, the inner needle 16 penetrates the main body 32 in an axial direction. The cylindrical portion 36 may be disposed between the main body 32 and the fixing portion 34, or base. In one embodiment, the cylindrical portion 36 may have an outer diameter that is less than an outer diameter of the fixing portion 34.

At least a part of an outer peripheral surface 33 of the main body 32 is inclined with respect to a central axis a of the valve body 20. At least a part of an inner peripheral surface in an internal space 32s of the main body 32 is inclined with respect to the central axis a. Specifically, the main body 32 includes a pair of inclined portions 38 formed on opposite sides with respect to the central axis a of the valve body 20. A distal end wall portion 32w (refer also to FIG. 4) is provided at a distal end of the pair of inclined portions 38.

Each inclined portion 38 includes an inclined outer surface 40 and an inclined inner surface 42 inclined so as to approach the central axis a of the valve body 20 in the distal direction. Therefore, the main body 32 includes a pair of inclined outer surfaces 40 and a pair of inclined inner surfaces 42. The inclined outer surface 40 forms a part of the outer peripheral surface 33 of the main body 32. The inclined inner surface 42 forms a part of the inner peripheral surface of the main body 32. The inclined outer surface 40 and the inclined inner surface 42 are flat surfaces in a natural state (e.g., in a state in which no external force acts upon the main body 32).

FIG. 2 also illustrates various additional features described in more detail below. In more detail, FIG. 2 shows that in a state where the valve body 20 is fixed in the catheter hub 14, an entirety of the (hollow) main body 32 and an entirety of the cylindrical portion 36 are spaced apart from an inner peripheral surface 14s (at 14s1) of the catheter hub 14. In addition, the inner peripheral surface 14s of the catheter hub 14 comprises a second groove 72 that engages with the fixing portion 34 to fix the valve body 20 in the catheter hub 14. In the state where the valve body 20 is fixed in the catheter hub 14, a first surface 74 of the second groove 72 contacts a first surface 76 of the fixing portion 34. In the state where the valve body 20 is fixed in the catheter hub 14, a second surface 78 of the second groove 72 connected to the first surface 74 of the second groove 72 contacts a second surface 80 of the fixing portion 34. In the state where the valve body 20 is fixed in the catheter hub 14, the first surface 74 of the second groove 72 is closer to the distal end of the valve body 20 than the second surface 78 of the second groove 72.

As shown, the fixing portion 34 comprises a third surface 82 that is exposed to a lumen 84 of the catheter hub 14. As also shown, the second surface 80 of the fixing portion 34 connects the first and third surfaces 76 and 82 of the fixing portion 34. Further, the inner peripheral surface 14s of the catheter hub 14 comprises a first inclined portion 86 extending from an end of the second surface 78 of the second groove 72 and that is exposed to the lumen 84 of the catheter hub 14. As shown, the first inclined portion 86 is inclined in a direction away from the third surface 82 of the fixing portion 34 and toward the central axis a of the valve body 20 when moving in a first direction that is away from the distal end of the valve body 20. In the example shown, the first inclined portion 86 extending from the end of the second surface 78 of the second groove 72 is inclined at a different angle with respect to the central axis a of the valve body 20 compared to the first and second surfaces 74 and 78 of the second groove 72. As further shown, the inner peripheral surface 14s of the catheter hub 14 comprises a second inclined portion 88 extending from an end of the first inclined portion 86. The second inclined portion 88 is inclined away from the central axis a of the valve body 20 when moving in the first direction.

Figure 3:
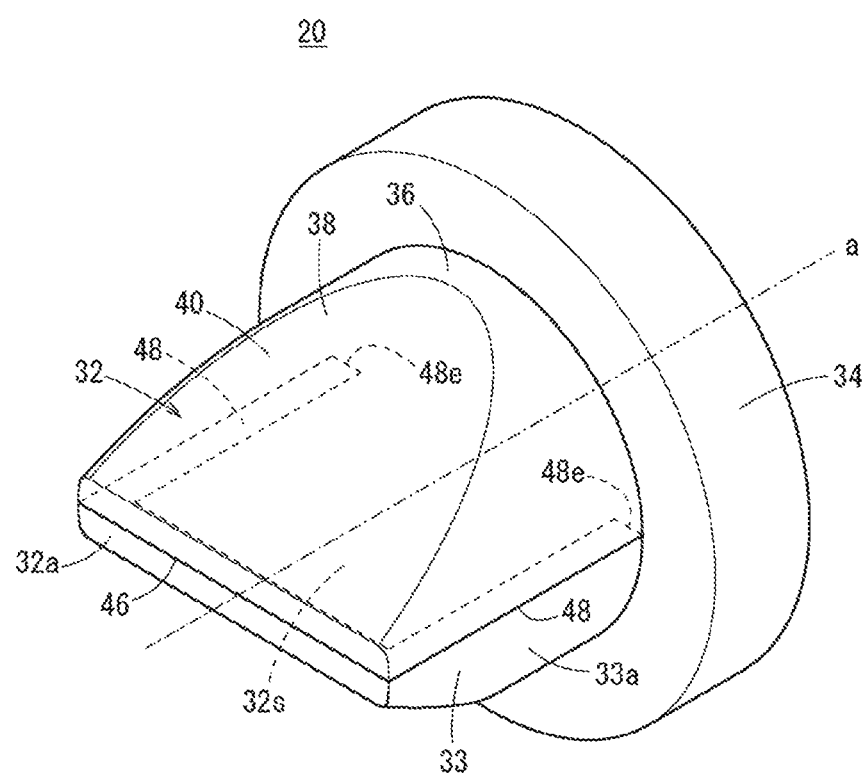
FIG. 3 is a perspective view of a valve body in accordance with embodiments of the present disclosure.

As illustrated in FIG. 3, the inclined outer surface 40 has a width which decreases in the proximal direction. The outer peripheral surface 33 of the main body 32 includes a cylindrical surface 33a. In this embodiment, the distal end surface 32a of the main body 32 is a flat surface formed into a substantially rectangular shape and is perpendicular to the central axis a. A short side of the distal end surface 32a is continuous to a distal end of the cylindrical surface 33a. A long side of the distal end surface 32a is continuous to a distal end of the inclined outer surface 40.

The fixing portion 34 is formed into a circular ring shape. An outer diameter of the fixing portion 34 is larger than a maximum outer diameter of the main body 32. Therefore, the fixing portion 34 has a shape protruding radially outward at the proximal end of the valve body 20. As illustrated in FIG. 2, the fixing portion 34 engages with a fixing groove 44 provided on an inner peripheral surface 14s of the catheter hub 14, so that the valve body 20 is fixed in a predetermined position in the catheter hub 14. In FIG. 2, the main body 32 and the cylindrical portion 36 are separated from an inner peripheral surface 14s1 on the distal end side with respect to the fixing portion 34 out of the inner peripheral surface 14s of the catheter hub 14 over an entire circumference.

The cylindrical portion 36 forms a portion between the main body 32 and the fixing portion 34. The cylindrical portion 36 and the fixing portion 34 form a base of the valve body 20. The cylindrical portion 36 is formed to be thinner than the fixing portion 34. Specifically, an outer diameter of the cylindrical portion 36 is constant in the axial direction and is smaller than the outer diameter of the fixing portion 34. The outer diameter of the cylindrical portion 36 is the same as the maximum outer diameter of the main body 32. An inner diameter of the cylindrical portion 36 is constant in the axial direction and is the same as an inner diameter of the fixing portion 34. Note that the inner diameter of the cylindrical portion 36 may be different from the inner diameter of the fixing portion 34.

Figure 4:
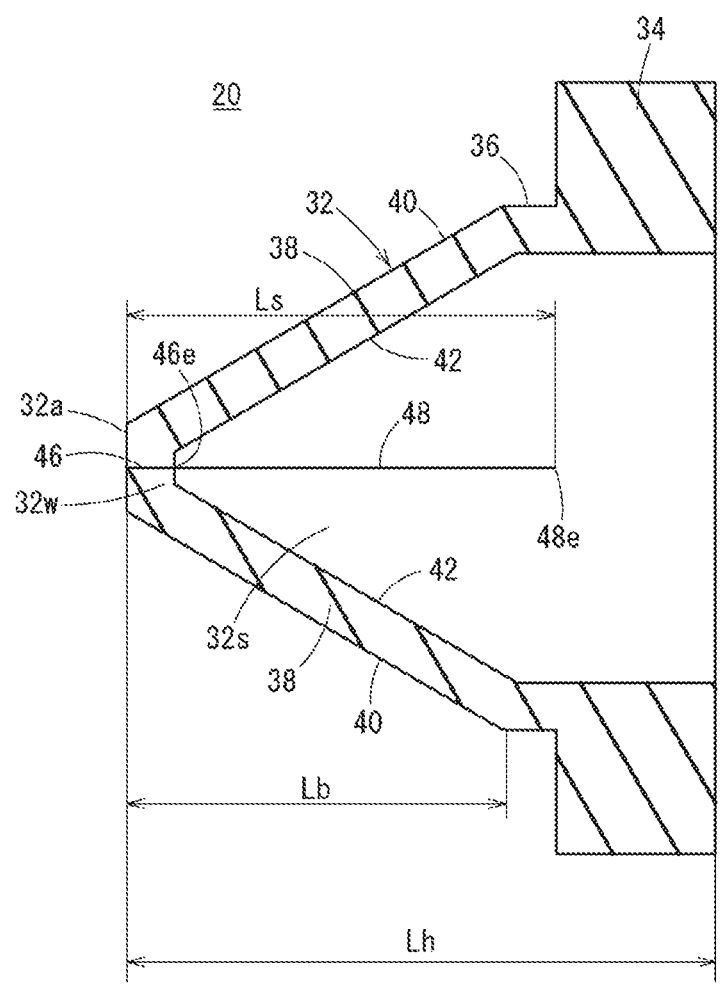
FIG. 4 is a cross-sectional view of the valve body shown in FIG. 3.

As illustrated in FIG. 3, the main body 32 includes a distal end slit 46 provided on the distal end surface 32a and a side slit 48 provided on the outer peripheral surface 33 of the main body 32 and continuously extending from the distal end slit 46. The distal end slit 46 extends in a direction orthogonal to the central axis a of the valve body 20 and both ends thereof reach the outer peripheral surface 33 of the main body 32. As illustrated in FIG. 4, the distal end slit 46 reaches a proximal end surface of the distal end wall portion 32w of the main body 32. Therefore, a proximal end 46e of the distal end slit 46 faces the internal space 32s of the main body 32.

As illustrated in FIG. 3, the side slit 48 extends in the proximal direction along the outer peripheral surface 33 of the main body 32 from both ends of the distal end slit 46. Therefore, a pair of side slits 48 are provided. Each side slit 48 reaches the inner peripheral surface of the main body 32 (e.g., faces the internal space 32s).

In this embodiment, the pair of side slits 48 extend from both the ends of the distal end slit 46 so as to be orthogonal thereto in parallel with each other with the same length. Note that, depending on a shape of the main body 32, the pair of side slits 48 may extend so as to be non-parallel to each other. The pair of side slits 48 may extend so as to be non-parallel to the central axis a of the valve body 20. The pair of side slits 48 may be formed with different lengths.

As illustrated in FIG. 4, a proximal end 48e of the side slit 48 is located at a proximal end of the cylindrical portion 36 (e.g., at the distal end of the fixing portion 34). Therefore, in this embodiment, a total length Ls of the side slit 48 in the axial direction of the valve body 20 is longer than a total length Lb of the main body 32 and shorter than a total length Lh of the valve body 20.

As illustrated in FIGS. 5A and 5B, the proximal end 48e of the side slit 48 may also be located on the distal end side with respect to the distal end of the fixing portion 34. In FIGS. 5A and 5B, the proximal end 48e of the side slit 48 is located on the distal end side with respect to a proximal end of the main body 32 (e.g., the distal end of the cylindrical portion 36). More specifically, in FIG. 5A, the proximal end 48e of the side slit 48 is located on the proximal end side with respect to the central position in the axial direction of the main body 32 (e.g., between the central position in the axial direction of the main body 32 and the proximal end of the main body 32). In FIG. 5B, the proximal end 48e of the side slit 48 is located on the distal end side with respect to the central position in the axial direction of the main body 32 (between the proximal end surface of the distal end wall portion 32w and the central position in the axial direction of the main body 32).

Figure 6A:
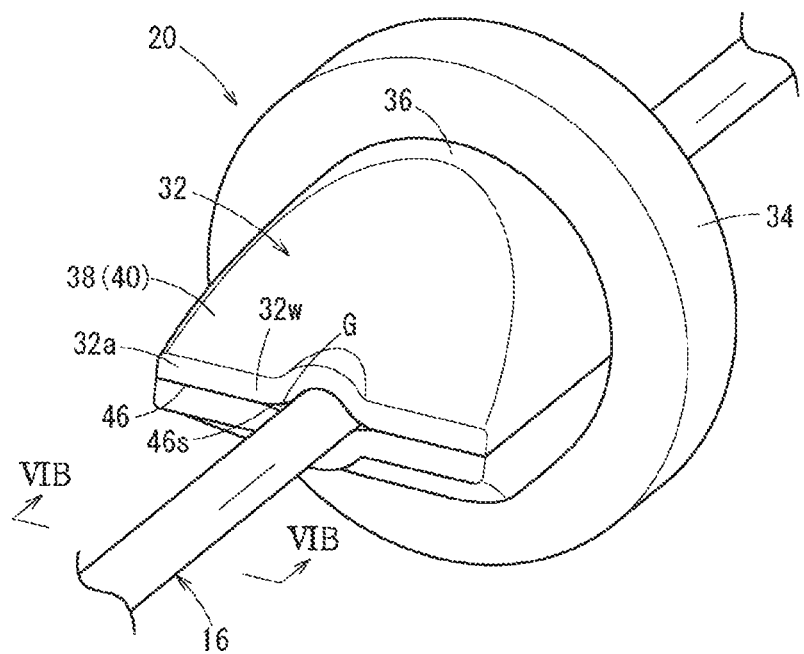
FIG. 6A is a perspective view illustrating the valve body in a state in which an inner needle inserts through the same.
Figure 6B:
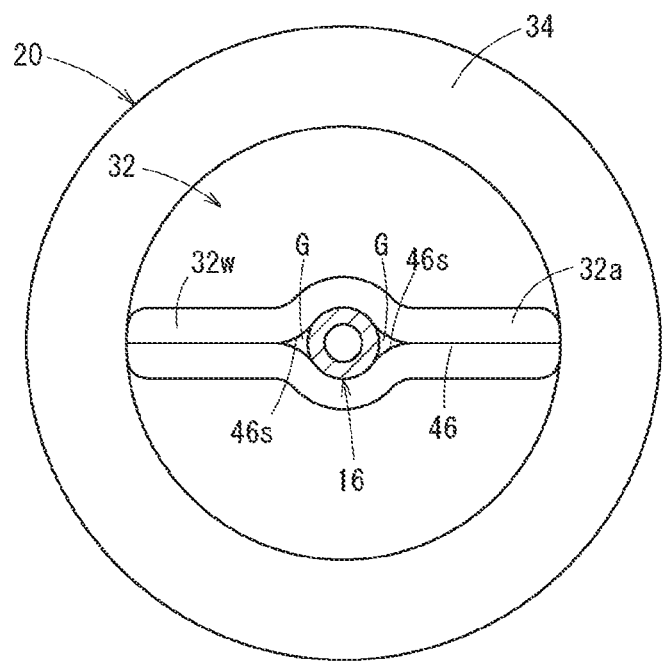
FIG. 6B is a cross-sectional view taken along line VIB-VIB in FIG. 6A.

As illustrated in FIGS. 6A and 6B, in a state in which the inner needle 16 penetrates the valve body 20 (e.g., in an initial state of the catheter assembly 10), a site of the distal end wall portion 32w of the valve body 20 which the inner needle 16 penetrates curves with elastic deformation. That is, the distal end wall portion 32w is pushed outward by the inner needle 16. Therefore, a triangular gap G is formed between slit surfaces 46s which form the distal end slit 46 and an outer peripheral surface of the inner needle 16. The gap G is formed in two sites opposite to each other across the inner needle 16. The gap G is formed so that gas (air) may pass therethrough. The gap G may be set to a size such that liquid (blood) passes therethrough with difficulty. Note that, in the state in which the inner needle 16 inserts into the valve body 20, it is possible that no gap is formed between the slit surfaces 46s and the outer peripheral surface of the inner needle 16 (e.g., the slit surface 46s may come into contact with the outer peripheral surface of the inner needle 16 over an entire circumference of the inner needle 16). The gap G may extend over an entire distal end slit 46. Furthermore, the gap G may extend to a distal end of the side slit 48.

Next, an action of the catheter assembly 10 configured as described above is described.

When the catheter assembly 10 is used, the user (doctor, nurse or the like) grips the needle hub 18 of the catheter assembly 10 in the initial state illustrated in FIG. 1 and punctures the blood vessel of the patient with the distal end portion of the catheter assembly 10 (e.g., the distal ends of the inner needle 16 and the catheter 12). With the puncture, the blood of the patient flows into the groove 26 formed at the distal end of the inner needle 16 (e.g., where flashback occurs). As a result, it is confirmed that the distal end of the catheter 12 secures the blood vessel. After the puncture, by pushing the catheter hub 14 in the distal direction while maintaining the positions of the needle hub 18 and the inner needle 16, the catheter 12 is advanced to be inserted into the blood vessel.

After the catheter 12 is inserted into the blood vessel by a predetermined length, the needle hub 18 is next pulled in the proximal direction in a state in which the position of the catheter member 22 is maintained, and the inner needle 16 is removed from the catheter member 22. At that time, the inner needle 16 is removed from the valve body 20. As a result, the catheter member 22 is indwelled in the patient side. After removing the inner needle 16 from the catheter member 22, the catheter hub 14 is fixed to the patient with the dressing material, tape or the like.

Figure 7:
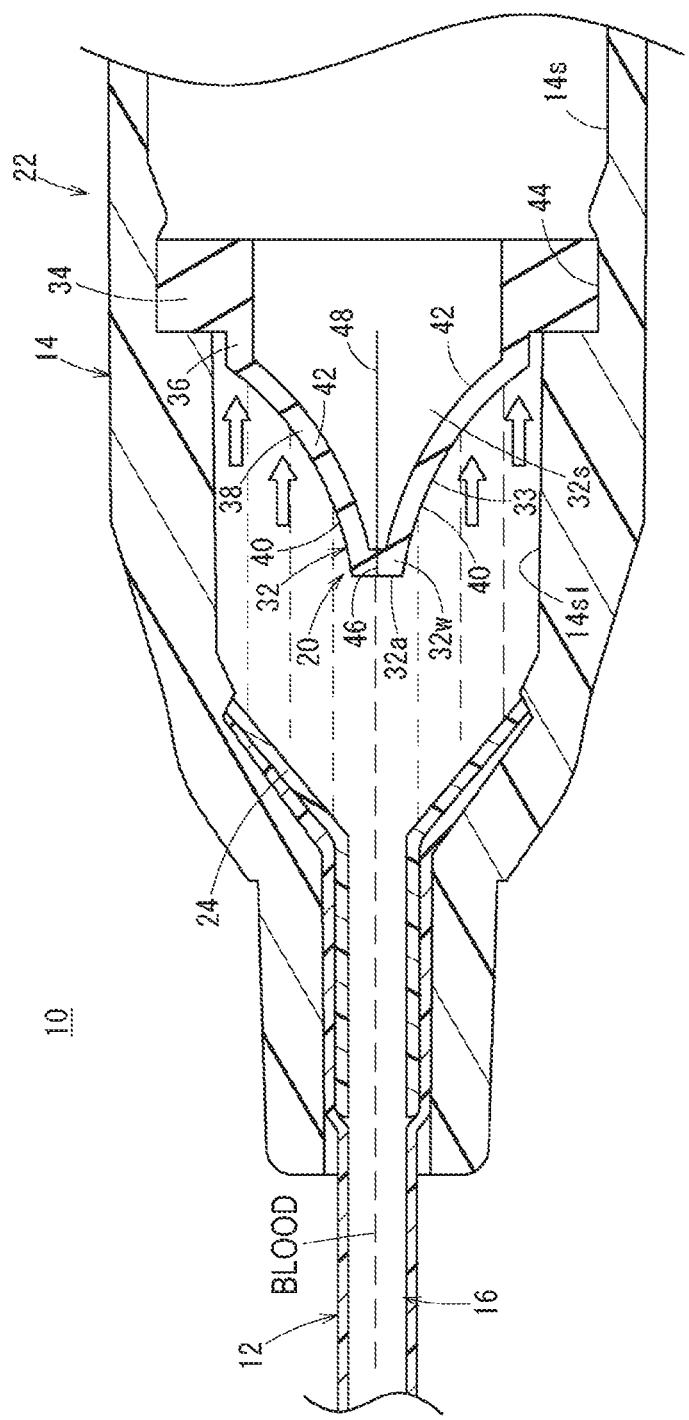
FIG. 7 is a partial cross-sectional view illustrating a closure state of the valve body in accordance with embodiments of the present disclosure.

Since the valve body 20 is provided in the catheter hub 14, the blood outflow from the catheter hub 14 is prevented even after the inner needle 16 is removed from the valve body 20. That is, as illustrated in FIG. 7, when the blood flows into the catheter hub 14 via the catheter 12 and a blood pressure is applied to the main body 32 of the valve body 20 from the distal end side of the valve body 20, the main body 32 (inclined portion 38) receives an inward force. As a result, the valve body 20 is closed, and the flow of the blood from the distal end side to the proximal end side of the valve body 20 is prevented or suppressed.

Next, a connector of a transfusion tube not illustrated is connected to a proximal end side of the catheter member 22 in a state in which the inner needle 16 is removed (e.g., from the proximal end of the catheter hub 14), and the drug solution (e.g., a transfusion material) is administered from the transfusion tube to the patient.

Figure 8:
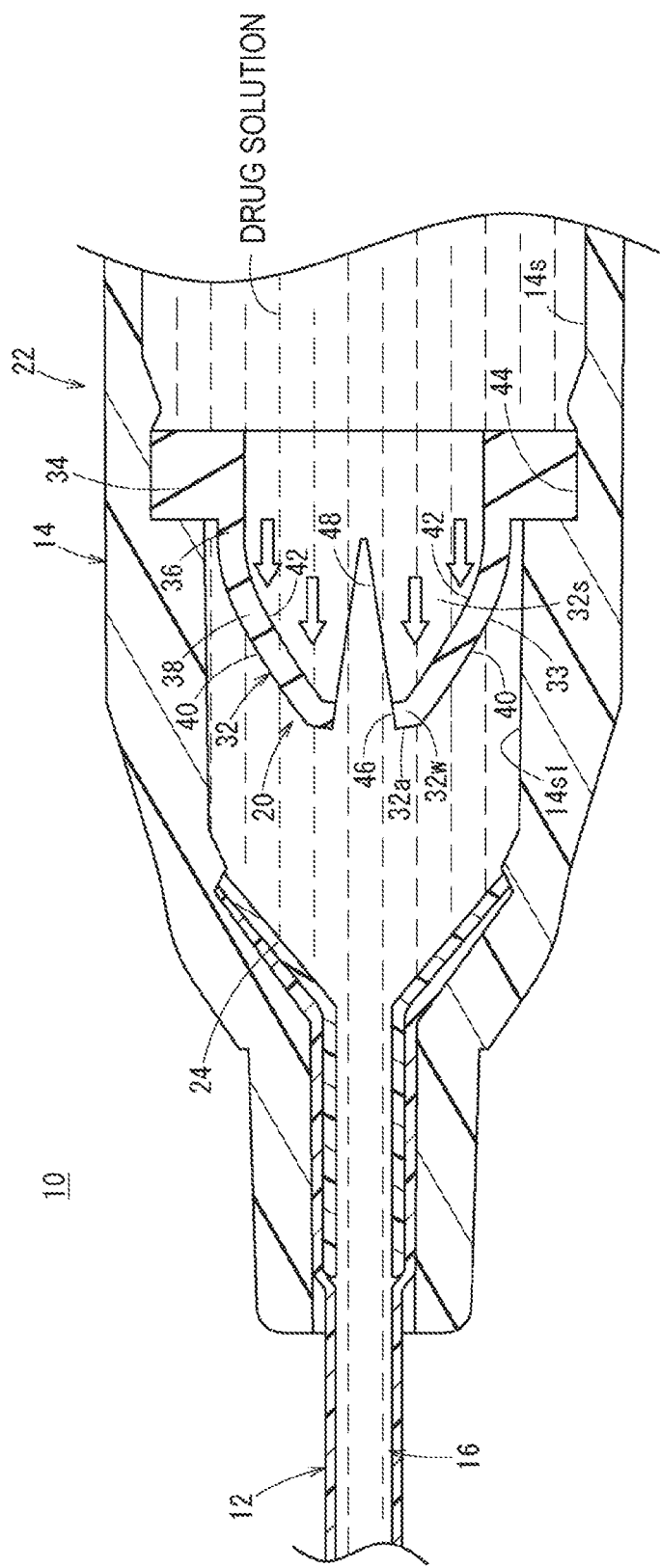
FIG. 8 is a partial cross-sectional view illustrating an opening state of the valve body in accordance with embodiments of the present disclosure.

When the drug solution is supplied from a proximal end side of the catheter hub 14 into the catheter hub 14, a drug solution pressure is applied to the main body 32 of the valve body 20 from the proximal end side of the valve body 20 as illustrated in FIG. 8. Then, the main body 32 (e.g., the inclined portion 38) receives an outward force. As a result, the valve body 20 is opened, and the flow of the drug solution from the proximal end side to the distal end side of the valve body 20 is allowed.

In this case, the catheter assembly 10 according to this embodiment has the following non-limiting effects.

According to the catheter assembly 10, as illustrated in FIG. 3, the main body 32 of the valve body 20 is provided with not only the distal end slit 46 but also the side slit 48 continuously extending from the distal end slit 46, so that the main body 32 is easily deformed when the pressure (e.g., via blood pressure and/or drug solution pressure, etc.) is applied to the main body 32. Therefore, as illustrated in FIG. 7, when the blood pressure is applied to the main body 32 from the distal end side, the main body 32 is deformed inward and the distal end slit 46 and the side slit 48 close, so that a blood backflow may be suppressed or prevented. In contrast, as illustrated in FIG. 8, when the drug solution pressure is applied to the main body 32 from the proximal end side, the main body 32 is deformed outward and not only the distal end slit 46 but also the side slit 48 opens, so that a flow rate at the time of opening may be increased. Therefore, according to the present disclosure, it is not necessary to use a separate component (plug) for opening, and it is possible to increase the flow rate at the time of opening without requiring a structure that is typically used to open a conventional duckbill valve.

Especially, in this embodiment, as illustrated in FIG. 3, the pair of side slits 48 are continuous from both the ends in a slit length direction of the distal end slit 46. With this configuration, when the pressure is applied from the distal end side or the proximal end side of the valve body 20, the main body 32 is more easily deformed inward or outward, respectively. Therefore, a function as the check valve (e.g., the function of stopping or suppressing the blood and function of allowing the drug solution to flow therethrough) for the valve body 20 may be further improved over conventional valves and assemblies.

The valve body 20 includes the cylindrical portion 36 formed to be thinner than the fixing portion 34 between the main body 32 and the fixing portion 34. With this configuration, the proximal end of the main body 32 is not directly connected to the distal end of the fixing portion 34 but is connected to a thinner cylindrical portion 36, so that the main body 32 is more easily deformed when the pressure is applied to the main body 32.

As illustrated in FIG. 4, the proximal end 48e of the side slit 48 is located at the proximal end of the cylindrical portion 36. With this configuration, the main body 32 is more easily deformed, so that the function as the check valve (e.g., the function of stopping or suppressing the blood and function of allowing the drug solution to flow) may be further improved.

As illustrated in FIGS. 6A and 6B, in a state in which the inner needle 16 inserts into the valve body 20, the gap G is formed between the slit surfaces 46s which form the distal end slit 46 and the outer peripheral surface of the inner needle 16. With this configuration, at the time of the puncture of the blood vessel with the distal end of the catheter assembly 10, it is possible to allow air to flow from the distal end side to the proximal end side of the valve body 20 through the gap G formed between the slit surfaces 46s and the inner needle 16. As a result, the catheter hub 14 may be vented before the inner needle 16 is removed from the catheter 12, and the distal end side with respect to the valve body 20 in the catheter hub 14 may be filled with the blood.

Figure 9:
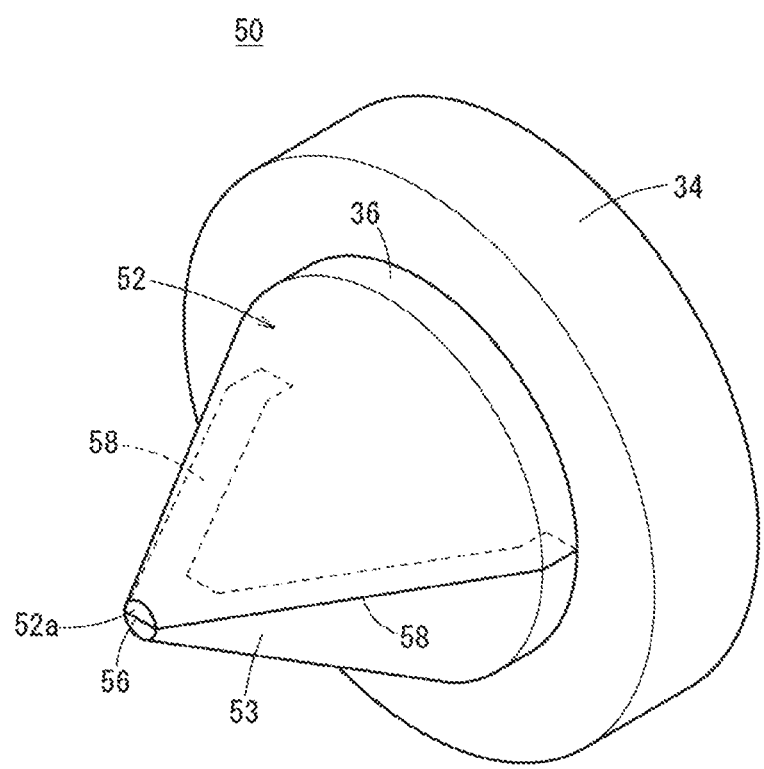
FIG. 9 is a perspective view of a valve body according to one embodiment of the present disclosure.

In the catheter assembly 10 described above, instead of the valve body 20, a valve body 50 provided with a conical main body 52 illustrated in FIG. 9 may be used. A distal end slit 56 is provided on a distal end surface 52a of the main body 52. On an outer peripheral surface 53 (e.g., a conical surface) of the main body 52, side slits 58 extending continuously from both ends of the distal end slit 56 are provided. Therefore, also in a case where this valve body 50 is used, the effect similar to that in a case where the above-described valve body 20 is used may be obtained.

Figure 10:
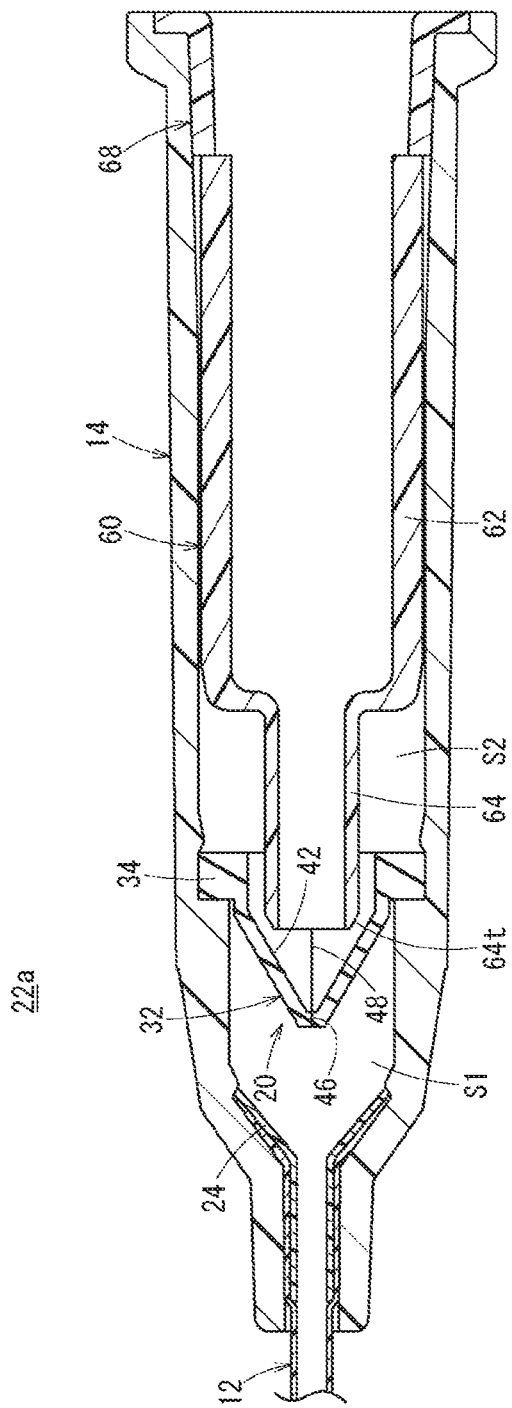
FIG. 10 is a cross-sectional view of a catheter member before opening a valve body according to an embodiment of the present disclosure.

In the catheter assembly 10 described above, a catheter member 22a illustrated in FIG. 10 may also be used. The catheter member 22a is provided with an opening member 60 arranged in a lumen of the catheter hub 14. The opening member 60 is a hollow plug arranged so as to be displaceable in the axial direction of the catheter hub 14 and is displaced in the distal direction with respect to the catheter hub 14 to open the valve body 20. As illustrated in FIG. 10, before the displacement in the distal direction (initial position), the opening member 60 is arranged in a proximal end side space S2 out of a distal end side space S1 and the proximal end side space S2 separated by the valve body 20 in the catheter hub 14.

The opening member 60 includes a hollow body portion 62 which forms a proximal end side of the opening member 60 and a hollow cylindrical pressing portion 64 which forms a distal end side of the opening member 60. The body portion 62 is supported by the inner peripheral surface of the catheter hub 14 and is slidable in the axial direction with respect to the inner peripheral surface of the catheter hub 14. The pressing portion 64 protrudes in the distal direction from a distal end of the body portion 62 and is formed to have a smaller diameter than that of the body portion 62. A distal end of the pressing portion 64 is inserted into the valve body 20 in an initial position illustrated in FIG. 10. A tapered portion 64t of the opening member 60, an outer diameter of which, decreases in the distal direction is provided at the distal end of the pressing portion 64.

An inner member 68 is fixed to the proximal end of the catheter hub 14. The inner member 68 restricts displacement of the opening member 60 from the initial position in the proximal direction with respect to the catheter hub 14. The inner member 68 is fitted to the lumen of the catheter hub 14 in a state of being located on the proximal end side with respect to the opening member 60 to be fixed with respect to the catheter hub 14.

Figure 11:
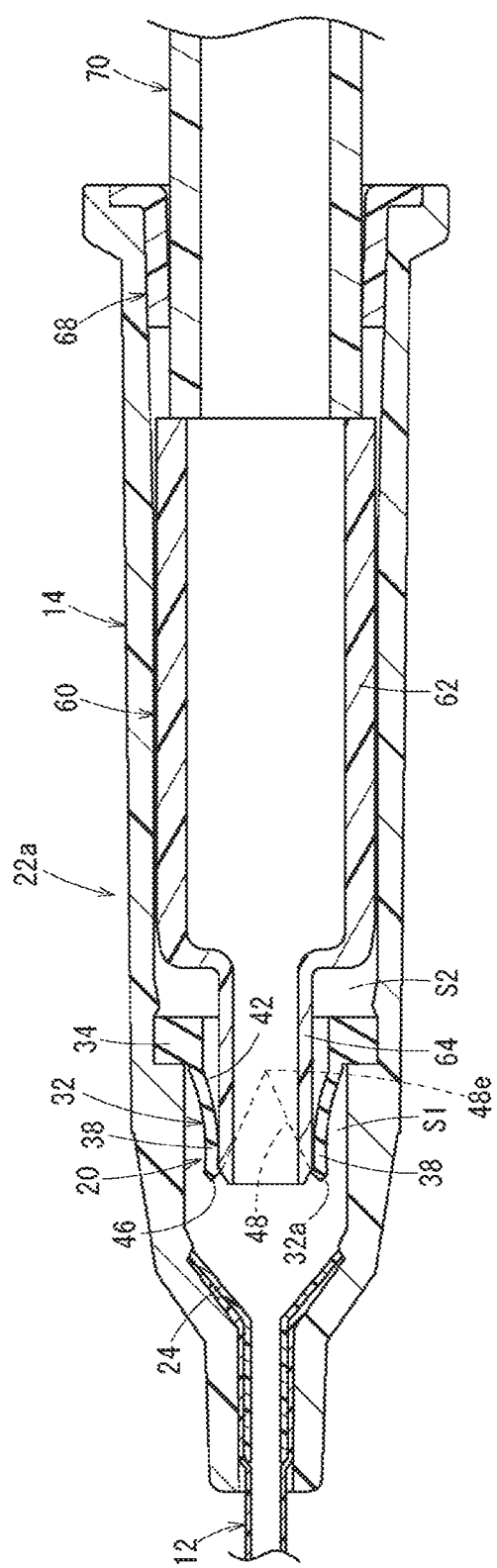
FIG. 11 is a cross-sectional view of the catheter member shown in FIG. 10 after opening the valve body.

When using the catheter assembly 10 in which the catheter member 22a configured in this manner is adopted, as illustrated in FIG. 11, after the inner needle 16 (FIG. 1) is removed from the catheter member 22a, the user attaches the connector 70 of the transfusion tube to a proximal end opening of the catheter hub 14 (inner member 68). A distal end of the connector 70 comes into contact with the proximal end of the opening member 60 at the time of insertion and pushes out the opening member 60 in the distal direction. The opening member 60 penetrates the distal end slit 46 of the valve body 20 as this moves (advances) in the distal direction. That is, the pressing portion 64 of the opening member 60 which advances abuts the inclined inner surface 42 of the main body 32 of the valve body 20 and pushes out the main body 32 from the inside. As a result, the main body 32 opens with elastic deformation. The distal end slit 46 of the valve body 20 is deformed along an outer shape of the opening member 60, and the gap of the side slit 48 is widened in the distal direction. Specifically, the side slit 48 of the pair of inclined portions 38 is deformed in an oblique direction with respect to an axis line from the proximal end 48e toward the distal end surface 32a. As a result, a lumen of the catheter 12, the lumen of the catheter hub 14, a lumen of the opening member 60, and a supply path of the connector 70 may be communicated with one another to deliver the transfusion material into the blood vessel of the patient.

According to a configuration obtained by combining the duckbill-type valve body 20 including the side slit 48 in addition to the distal end slit 46 and the opening member 60 just like the catheter member 22a, it is possible to open the valve body 20 even when a moving distance from when the opening member 60 starts pushing the valve body 20 is shorter than that in a case of a combination of a disc-shaped valve body (so-called disc valve) and the opening member 60. That is, since the valve body 20 is provided with the side slit 48, the distal end slit 46 and the side slit 48 start opening simply when the opening member 60 (pressing portion 64) pushes the main body 32 of the valve body 20 a little in the distal direction from the inside (the valve body 20 is half-open), so that the valve body 20 is opened quickly. According to the configuration of the combination of the valve body 20 and the opening member 60, the valve body 20 may be opened with a smaller force than that in a case of the combination of the disc valve and the opening member 60, so that the operation is easy. Note that, in the catheter member 22*a*, the valve body 50 (FIG. 9) may be used instead of the valve body 20.

The present disclosure is applicable to other medical valves arranged in a fluid passage of a medical device in addition to the valve bodies 20 and 50 for the catheter assembly 10 described above.

The present disclosure is not limited to the above-described embodiments, and various modifications may be made without departing from the scope of the present disclosure.

What is claimed is:

1. A catheter assembly comprising:
   a catheter;
   a catheter hub fixed to the catheter;
   a valve body provided in the catheter hub; and
   an opening member and an inner member,
   wherein the valve body includes a hollow main body provided with a distal end surface located at a distal end of the valve body, and a fixing portion for fixing the valve body to the catheter hub,
   wherein at least a part of an outer peripheral surface of the hollow main body is inclined with respect to a central axis of the valve body,
   wherein at least a part of an inner peripheral surface in an internal cavity of the hollow main body is inclined with respect to the central axis,
   wherein the hollow main body includes a distal end slit provided on the distal end surface and a side slit provided on the outer peripheral surface of the hollow main body and continuously extending from the distal end slit,
   wherein the fixing portion comprises a proximal surface that is exposed to a lumen of the catheter hub in a state where the valve body is fixed in the catheter hub,
   wherein, in a cross-sectional view taken along a direction that is perpendicular to the distal end of the valve body, one side of an inner surface of the valve body has a first surface portion that connects a second surface portion that is parallel to the central axis of the valve body to a third surface portion that is perpendicular to the central axis of the valve body,
   wherein a first transition between the first surface portion and the second surface portion forms a first inward facing obtuse angle,
   wherein a second transition between the first surface portion and the third surface portion forms a second inward facing obtuse angle,
   wherein the second surface portion extends from the proximal surface of the fixing portion to the first surface portion,
   wherein the third surface portion of the inner surface of the valve body is opposite the distal end surface of the hollow main body,
   wherein the opening member comprises:
      a hollow cylindrical pressing portion which forms a distal side of the opening member;
      a hollow body portion extending proximally from the hollow cylindrical pressing portion;
      a proximal portion of the opening member which is supported by an inner peripheral surface of the catheter hub and is slidable in an axial direction with respect to the inner peripheral surface of the catheter hub; and
      a distal end of the hollow cylindrical pressing portion which is disposed in the internal cavity of the hollow main body of the valve body in an initial state in which no external force acts upon the opening member, and
   wherein the inner member comprises:
      a cylindrical body which is fitted to the inner peripheral surface of the catheter hub;
      an inner cavity into which a connector of an infusion tube can be attached;
      a distal portion; and
      a distal end surface that is arranged to abut against the proximal portion of the opening member in the initial state in which no external force acts upon the opening member, wherein the proximal portion of the opening member comprises an opening member proximal protruding portion which protrudes inwardly from the distal portion of the inner member in the initial state so that the opening member proximal protruding portion contacts a tip surface of the connector in a connector insertion state.

2. The catheter assembly of claim 1, wherein:
   the valve body includes a cylindrical portion extending between the hollow main body and the fixing portion;
   the cylindrical portion has a constant outer diameter along the central axis of the valve body;
   the valve body has a pair of flat surfaces with no slits in a state in which no external force acts upon the main body, and each flat surface is between a pair of curved surfaces in a circumferential direction of the valve body; and
   the side slit terminates at a boundary between the fixing portion and the cylindrical portion, the side slit is disposed along the pair of curved surfaces parallel to the central axis of the valve body.

3. The catheter assembly of claim 2, wherein:
   the pair of flat surfaces each comprise a proximal end;
   the side slit extends further than the proximal end of each flat surface along the central axis of the valve body.

4. The catheter assembly of claim 1, wherein the inner member comprises a proximal end including a flange shaped end covering a proximal end of the catheter hub.

\* \* \* \* \*